United States Patent
Kessler et al.

(10) Patent No.: US 10,001,466 B2
(45) Date of Patent: Jun. 19, 2018

(54) MAGNIFYING DEVICE FOR JEWELRY AND SYSTEM FOR USE OF SAME

(71) Applicant: Sy Kessler Sales, Inc., Dallas, TX (US)

(72) Inventors: Daniel L. Kessler, Dallas, TX (US); Henry M. Kessler, Dallas, TX (US)

(73) Assignee: Sy Kessler Sales, Inc., Dallas, TX (US)

( * ) Notice: Subject to any disclaimer, the term of this patent is extended or adjusted under 35 U.S.C. 154(b) by 86 days.

(21) Appl. No.: 15/278,446

(22) Filed: Sep. 28, 2016

(65) Prior Publication Data

US 2017/0089880 A1 Mar. 30, 2017

Related U.S. Application Data

(60) Provisional application No. 62/233,481, filed on Sep. 28, 2015.

(51) Int. Cl.
| | |
|---|---|
| *G01N 33/38* | (2006.01) |
| *G02B 25/00* | (2006.01) |
| *G02B 7/02* | (2006.01) |
| *G01N 25/18* | (2006.01) |
| *G01N 27/04* | (2006.01) |

(52) U.S. Cl.
CPC ........... *G01N 33/381* (2013.01); *G01N 25/18* (2013.01); *G02B 7/026* (2013.01); *G02B 25/002* (2013.01); *G01N 27/041* (2013.01)

(58) Field of Classification Search
USPC ........................................ 324/71.1, 717, 724
See application file for complete search history.

(56) References Cited

U.S. PATENT DOCUMENTS

| | | |
|---|---|---|
| 889,352 A | 6/1908 | Bold |
| 2,649,838 A | 5/1949 | Krause et al. |
| 3,007,566 A | 11/1961 | Morris |
| 3,955,884 A * | 5/1976 | Del Pesco, Sr. ..... G02B 25/005 |
| | | 359/804 |
| 4,763,986 A | 8/1988 | Sego |
| 4,770,635 A | 9/1988 | Gabay |
| 7,000,291 B2 | 2/2006 | Fuller |
| 2005/0071956 A1 | 4/2005 | Fuller |
| 2012/0007619 A1 * | 1/2012 | Zhu ........................ G01N 25/18 |
| | | 324/717 |
| 2014/0152955 A1 | 6/2014 | Papageorgiou et al. |
| 2015/0153233 A1 | 6/2015 | Broyer |

* cited by examiner

*Primary Examiner* — Vincent Q Nguyen

(74) *Attorney, Agent, or Firm* — Scott T. Griggs; Griggs Bergen LLP

(57) ABSTRACT

A magnifying device for jewelry and system for use of the same are disclosed. In one embodiment of the magnifying device, a securing ring is coupled to a body to selectively attach in a snap-fit engagement with a gem tester. A hinge assembly is also coupled to the body and a support frame is pivotally coupled thereto. A seat within the support frame defines a circular opening securing a magnifying lens therein. The support frame also includes a pivot blade extending therefrom that accepts rotational bearing force to cause the support frame and therefore the magnifying lens to rotate relative to the body.

5 Claims, 3 Drawing Sheets

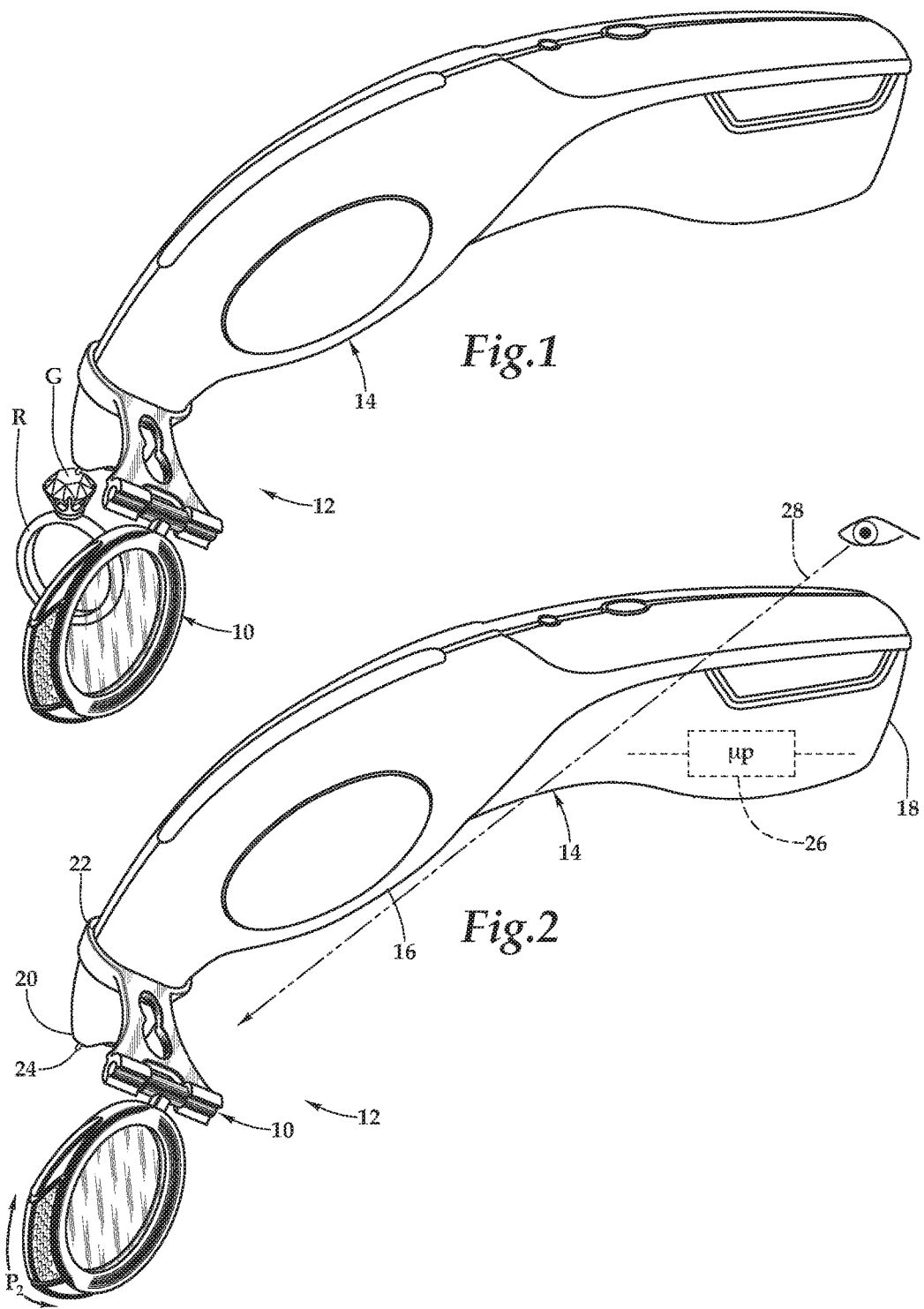

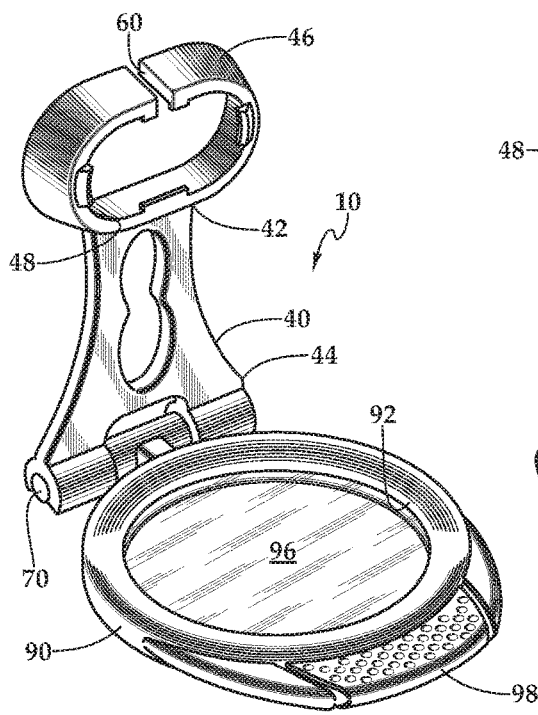
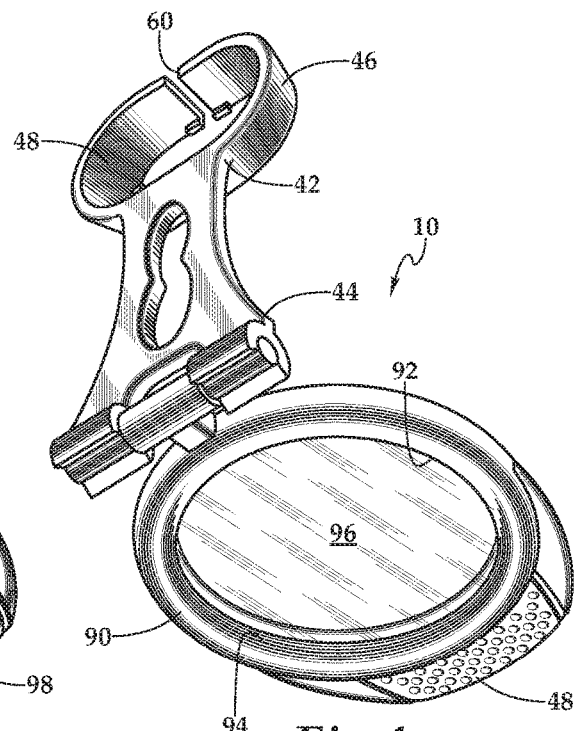
Fig.3                    Fig.4
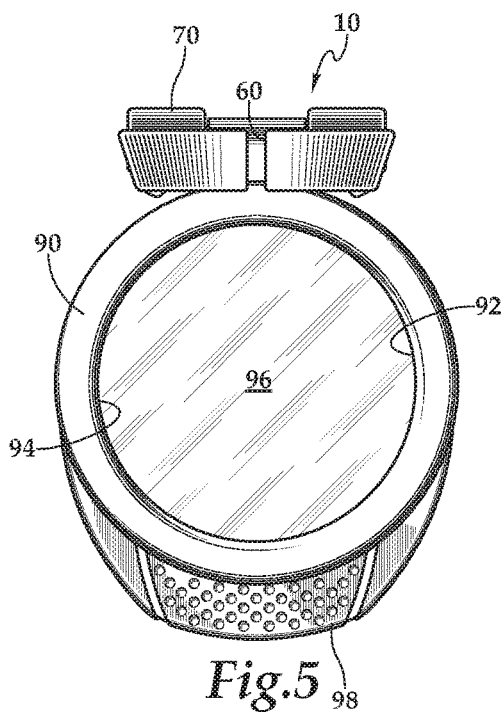
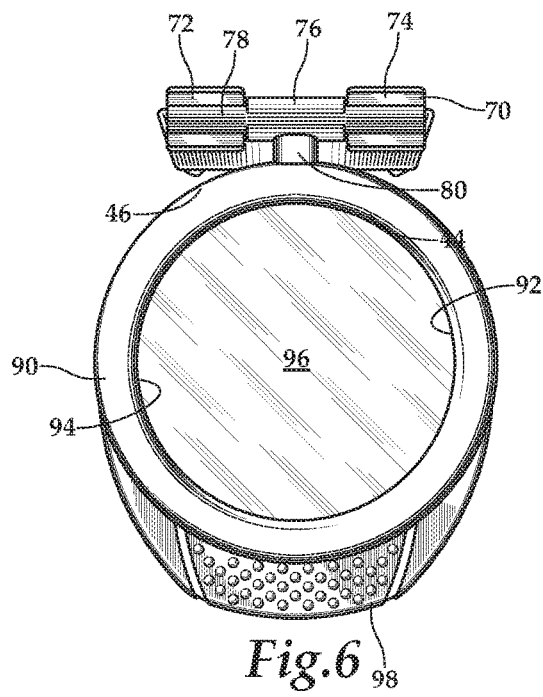
Fig.5                    Fig.6

MAGNIFYING DEVICE FOR JEWELRY AND SYSTEM FOR USE OF SAME

PRIORITY STATEMENT

This application claims priority from U.S. Patent Application Ser. No. 62/233,481 entitled "Magnifying Glass for Jewelry and System for Use of Same" and filed on Sep. 28, 2015, in the names of Daniel L. Kessler and Henry M. Kessler; which is hereby incorporated by reference for all purposes.

TECHNICAL FIELD OF THE INVENTION

This invention relates, in general, to magnifying glasses and, in particular, magnifying devices that are commonly carried and used by jewelers and the like, to examine jewelry and precious gems.

BACKGROUND OF THE INVENTION

Without limiting the scope of the present disclosure, its background will be discussed with reference to gemstones, as an example. Gemstones such as cubic zirconium and silicon carbide, commonly known as moissanite, have become more readily available and more indistinguishable from real diamonds. As a result, the market is flooded with moissanite which is passed off as diamond. Advances in instruments and techniques are required to authenticate diamonds and prevent fraudulent and mistaken sales.

SUMMARY OF THE INVENTION

It would be advantageous to achieve advances in instruments to authenticate diamonds in order to prevent fraudulent and mistaken sales. It would also be desirable to enable a mechanical solution that would improve operator technique when authenticating diamonds with a gem tester. To better address one or more of these concerns, a magnifying device for jewelry and system for use of the same are disclosed. In one embodiment of the magnifying device, a securing ring is coupled to a body to selectively attach in a snap-fit engagement with a gem tester. A hinge assembly is also coupled to the body and a support frame is pivotally coupled thereto. A seat within the support frame defines a circular opening securing a magnifying lens therein. The support frame also includes a pivot blade extending therefrom that accepts rotational bearing force to cause the support frame and therefore the magnifying lens to rotate relative to the body.

In one embodiment of a system for testing a gem under test, the system includes the magnifying device selectively and releasably attached to a gem tester, which may include an elongated body having a probe extending therefrom. A circuit portion located within the elongated body is thermo-electrically coupled to the probe to measure conductivity of the gem under test. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 1 is a side perspective view of one embodiment of a magnifying device being utilized with a gem tester to examine a gem under test according to the teachings presented herein;

FIG. 2 is a side elevation view of one embodiment of the magnifying device of FIG. 1 being utilized with a gem tester, depicted without a user's hand as shown in FIG. 1;

FIG. 3 is a front perspective view of the magnifying device depicted in FIG. 1;

FIG. 4 is a rear perspective view of the magnifying device depicted in FIG. 1;

FIG. 5 is a top plan view of the magnifying device shown in FIG. 1;

FIG. 6 is a bottom plan view of the magnifying device shown in FIG. 1;

DETAILED DESCRIPTION OF THE INVENTION

Figure 7:
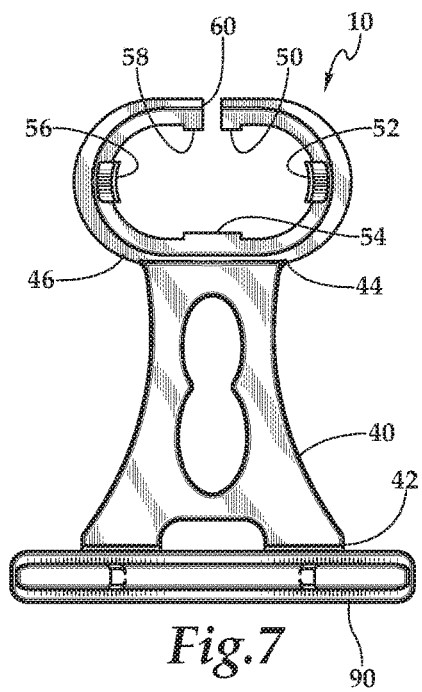
FIG. 7 is a front elevation view of the magnifying device shown in FIG. 1.

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Referring initially to FIGS. 1 and 2, therein is depicted a magnifying device that is schematically illustrated and generally designated 10. As shown, the magnifying device is being utilized within a system 12 having a gem tester 14 for testing a gem under test G and jewelry R. The gem tester 14 includes an elongated body 16 having ends 18, 20. A probe 24 extends from the end 18 of the elongated body 16. Within the probe 24, a circuit portion 26 is thermo-electrically coupled to the probe 24 to measure conductivity of the gem under test G and jewelry R. By way of example, the circuit portion 26 may be electrically coupled to the probe 24 to measure electrical conductivity of the gem under test G and the jewelry R. By way of further example, the circuit portion 26 may be thermally coupled to the probe 24 to measure thermal conductivity of the gem under test G and jewelry R. A viewing angle 28 intersects the magnifying device 10 when the magnifying device 10 is positioned in an operable configuration to give a user a magnified view of the gem under test G and the jewelry R.

By way of further example, the reading process of the gem tester 14 makes two measurements: thermal conductivity and electrical conductivity. The thermal conductivity test separates diamond from all known diamond simulants, except moissanite, since diamonds conduct heat significantly greater than all other gemstones, except moissanite. White sapphire is thermally conductive, yet not as conductive as diamond and moissanite and can be therefore easily be separated. Since moissanite conducts electricity in varying degrees and diamonds generally do not conduct electricity, the electrical conductivity test separates the vast majority of moissanite from diamond is the electrical conductivity test. Therefore, based upon readings from the conductivity and electrical tests, the type of gem or metal may be determined.

The magnifying device 10 magnifies the space beneath the magnifying device 10 and any object, such as a precious gem or jewelry placed in the space beneath the gem tester 14 so that a viewer can more readily observe all features of the gem G or jewelry R and via the magnification ensure proper and desired contract between the probe 24 and the gem G or jewelry R.

Figure 8:
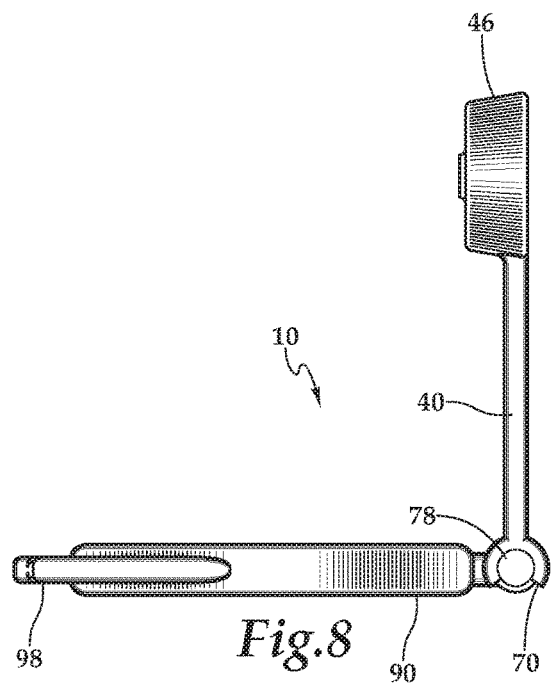
FIG. 8 is a left side elevation view of the magnifying device shown in FIG. 1.
Figure 9:
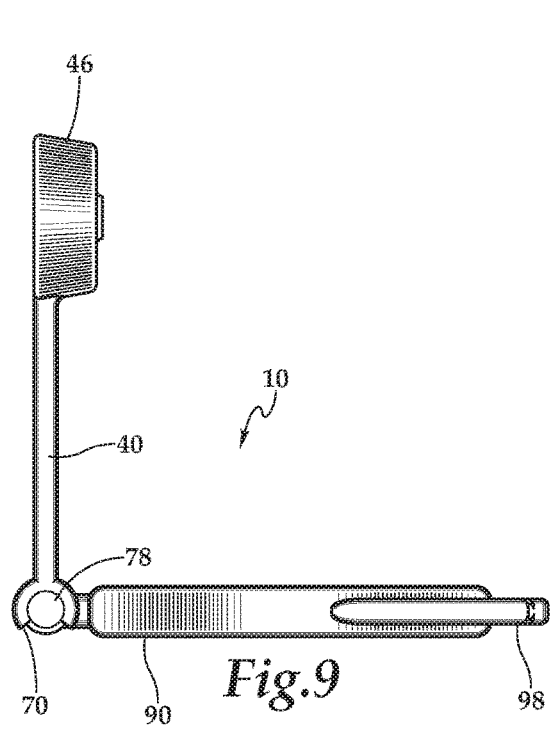
FIG. 9 is a right side elevation view of the magnifying device shown in FIG. 1.
Figure 10:
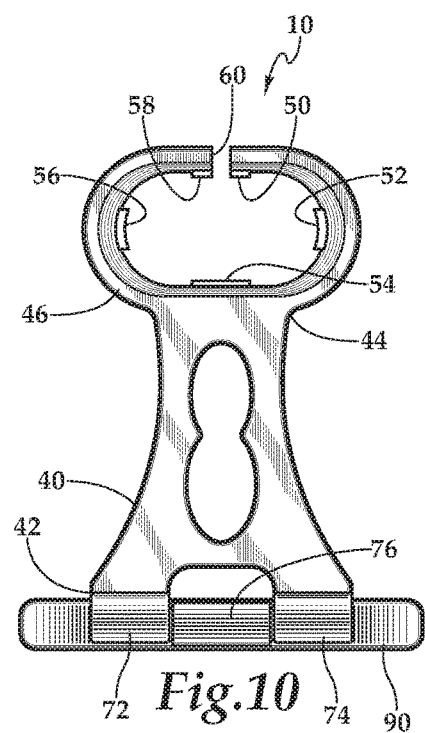
FIG. 10 is a rear elevation view of the magnifying device shown in FIG. 1.

Referring now to FIG. 3 through FIG. 10, in one embodiment, the magnifying device 10 includes a body 40 having a proximal end 42 and a distal end 44. A securing ring 46 may be coupled to the proximal end 42 of the body 40 and inscribed by a collar 48 having multiple detention tangs 50, 52, 54, 56, 58 thereon. As shown, the collar 48 may have five detention tangs. The collar 48 is sized to compliment in fit the neck 22 of the gem tester 14. An opening 60 is opposite a hinge assembly 70 and positioned to release pressure when the magnifying device 10 is selectively attached to the gem tester 14. The detention tangs 50, 52, 54, 56, 58 create a selectively attachable snap-fit engagement between the collar 48 and the neck 22. As shown, in one embodiment, the magnifying device 10 is symmetrical and may be coupled to the left side or right side of the gem tester 14. This symmetrical attachment facilitates use for left- or right-handed individuals. In this manner, the securing ring may be a symmetrical coupling coupled to the proximal end of the body, where the symmetrical coupling is sized to compliment in fit a neck of a gem tester and create a selectively attachable snap-fit engagement between the collar and the neck. Alternatively, the securing ring may be based on tension/friction, a mechanical fit, a magnetic fit, or other suitable fit.

The hinge assembly 70 is coupled to the distal end of the body 40. As depicted, the hinge assembly 70 includes two spaced hinge pads 72, 74 having a hinge bushing 76 interleaved therebetween. A hinge pin 78 traverses the hinge pad 72, hinge bushing 76, and hinge pad 74. A pivot arm 80 extends from the hinge bushing 76 in order to transfer rotational bearing force to cause the pivot arm 80 to rotate relative to the body 40. A support frame 90 is coupled to the pivot arm 80 and includes a seat 92 defining a circular opening 94 securing a magnifying lens 96 therein. The magnifying lens 96 may include glass, polymer, polycarbonate glass, of other suitable material and have a magnification from about 0.5× to about 20× or greater. The support frame 90 includes a pivot blade 98 extending therefrom that accepts rotational bearing force to cause the pivot arm 80 and support frame 90 to rotate relative to the body 40.

In using the magnifying device 10, the magnifying lens may be rotated (see arrow P in FIG. 2) and positioned such that a gem stone G being examined is within the natural and/or supplemental light falling thereon to provide for optimum viewing through the magnifying device 10. This enables a jeweler or other viewer to be able to determine all of the characteristics of the precious gem being examined. Further, when used in combination with the gem tester 14, the magnification assists the jeweler or viewer in ensuring the proper contact between the probe of the gem tester 14 and the gem under test G. As shown by arrow P in FIG. 2, when in use, the magnifying lens 96 of the magnifying device 10 is rotatable with internal and external rotation about an arc toward and away from an axis of the gem tester 14 and perpendicular to an axis of the body 40.

The order of execution or performance of the methods and process flows discussed and described herein is not essential, unless otherwise specified. That is, elements of the methods and process flows may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A system for testing a gem under test, the system comprising:
    a gem tester comprising:
        an elongated body having a first end and a second end,
        a probe extending from the first end of the elongated body,
        a circuit portion located within the elongated body, the circuit portion being thermo-electrically coupled to the probe to measure conductivity of the gem under test; and
    a magnifying device for a gem under test selectively attached to the gem tester, the magnifying device comprising:
        a body having a proximal end and a distal end,
        a securing ring coupled to the proximal end of the body, the securing ring inscribed by a collar having a plurality of detention tangs thereon, the collar sized to compliment in fit the elongated body proximate to the first end thereof, the plurality of detention tangs creating a selectively attachable snap-fit engagement between the collar and the elongated body proximate to the first end thereto,
        a hinge assembly coupled to the distal end of the body, the hinge assembly including spaced first and second hinge pads having a hinge bushing interleaved therebetween, the hinge assembly including a hinge pin traversing the first hinge pad, hinge bushing, and second hinge pad,
        the hinge assembly including a pivot arm extending from the hinge bushing, the pivot arm transferring rotational bearing force to cause the pivot arm to rotate relative to the body, and
        a support frame coupled to the pivot arm, the support frame including a seat defining a circular opening securing a magnifying lens therein, the support frame including a pivot blade extending therefrom, the pivot blade accepting rotational bearing force to cause the pivot arm and support frame to rotate relative to the body.

2. The system as recited in claim 1, wherein the circuit portion is electrically coupled to the probe to measure electrical conductivity of the gem under test.

3. The system as recited in claim 1, wherein the circuit portion is thermally coupled to the probe to measure thermal conductivity of the gem under test.

4. The system as recited in claim 1, wherein the plurality of detention tangs further comprise three detention tangs approximately equally spaced about the collar.

5. The system as recited in claim 1, wherein the collar further comprises an opening opposite the hinge assembly.

* * * * *